(12) United States Patent
Duconge et al.

(10) Patent No.: US 8,940,886 B2
(45) Date of Patent: Jan. 27, 2015

(54) SPECIFIC LIGAND FOR ANNEXIN 2

(75) Inventors: Frédéric Duconge, Sceaux (FR); Agnès Cibiel, Avon, CA (US)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 73 days.

(21) Appl. No.: 13/884,528

(22) PCT Filed: Nov. 10, 2011

(86) PCT No.: PCT/IB2011/055019
§ 371 (c)(1),
(2), (4) Date: Jun. 12, 2013

(87) PCT Pub. No.: WO2012/063219
PCT Pub. Date: May 18, 2012

(65) Prior Publication Data
US 2013/0266515 A1    Oct. 10, 2013

(30) Foreign Application Priority Data

Nov. 12, 2010    (FR) ..................................... 10 04412

(51) Int. Cl.
*C07H 21/04*    (2006.01)
*C07H 21/02*    (2006.01)
*C12N 15/115*    (2010.01)

(52) U.S. Cl.
CPC .............. *C07H 21/02* (2013.01); *C12N 15/115* (2013.01); *C12N 2310/16* (2013.01); *C12N 2310/344* (2013.01); *C12N 2310/351* (2013.01); *C12N 2310/3517* (2013.01)
USPC ...................................... 536/24.5

(58) Field of Classification Search
USPC ......................................................... 536/24.5
See application file for complete search history.

(56) References Cited

FOREIGN PATENT DOCUMENTS

WO    2005/093097    10/2005

OTHER PUBLICATIONS

Sharma, Angiogenesis-Associated Protein Annexin II in Breast Cancer: Selective Expression in Invasive Breast Cancer and Contribution to Rumor Invasion and Progression, Experimental and Molecular Pathology, 81, pp. 146-156, 2006.
Tavitian, In Vivo Imaging of Oligonucleotidic Aptamers, Methods in Molecular Biology, 525, pp. 241-259, 2009.
Li, A Cy5-Labeled S100A10 Tracer Used to Identify Inhibitors of the Protein Interaction with Annexin A2, Assay and Drug Development Technologies, 8, pp. 85-95, 2010.
Pestourie, Aptamers Against Extracellular Targets for in Vivo Applications, Biochimie, 87, pp. 921-930, 2005.
Kesavan, Annexin A2 is a Molecular Target for TM601, a Peptide with Tumor-Targeting and Anti-Angiogenic Effects, Journal of Biological Chemistry, 285, pp. 4366-4374, 2010.

*Primary Examiner* — Brian Whiteman
(74) *Attorney, Agent, or Firm* — Morgan, Lewis & Bockius LLP

(57) ABSTRACT

The present invention relates to an aptamer which includes a nucleic acid including or made up of: the sequence GGAACGCAAGAACUGAGGCCAUGAG-GCGCCUUCCCUUGCUCA GGACGC (SEQ ID NO: 1), or the sequence AGCUAGGCCGCAAGGUGCCUCAACGC-CAUCUGAGUGCCGACC CGAUCGC (SEQ ID NO: 2), or a sequence including or made up of at least 25 consecutive nucleotides of a sequence that is at least 80% identical to SEQ ID NO: 1 or to SEQ ID NO: 2, with the condition that a nucleic acid made up of said sequence is bonded to annexin 2.

11 Claims, 12 Drawing Sheets

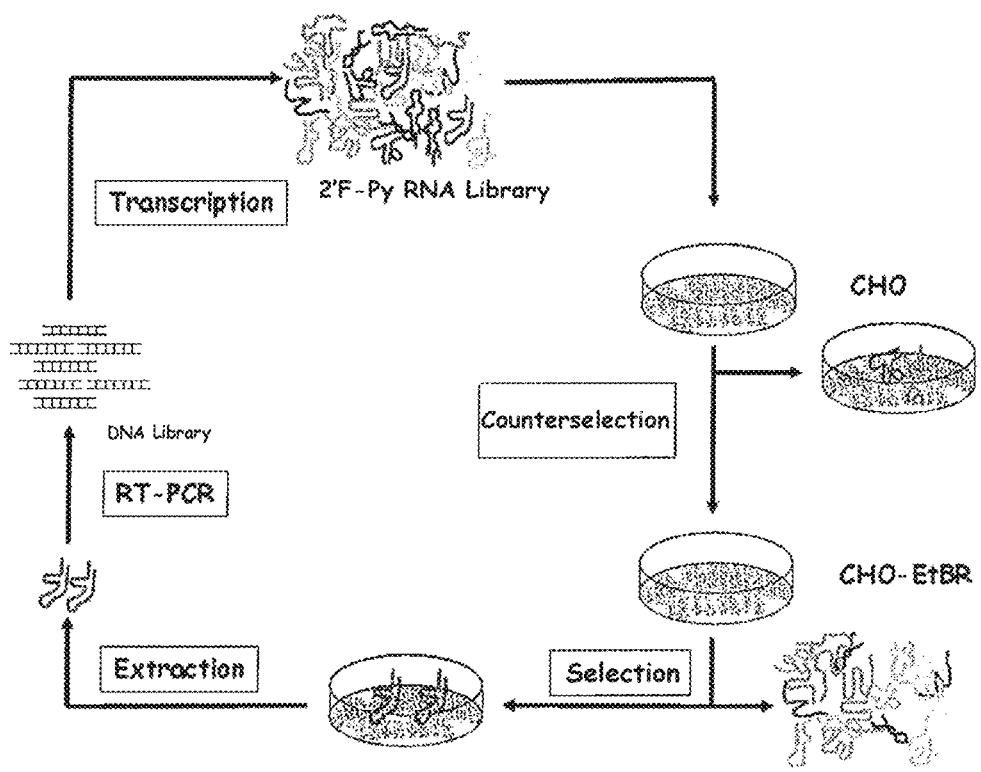
Figure 1
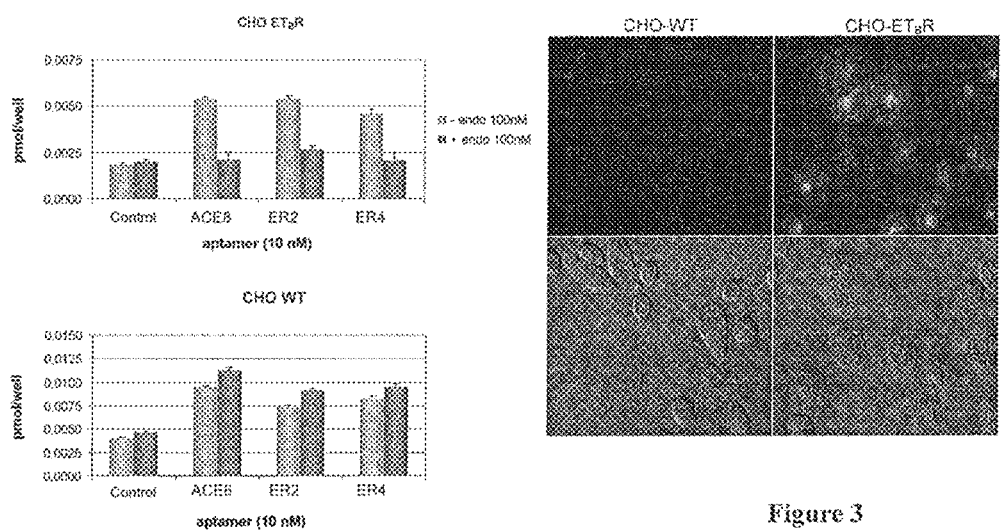
Figure 2
Figure 3

SPECIFIC LIGAND FOR ANNEXIN 2

SEQUENCE LISTING SUBMISSION VIA EFS-WEB

A computer readable text file, entitled "045636-5230_SequenceListing.txt," created on or about 9 May 2013, with a file size of about 6 kb contains the sequence listing for this application and is hereby incorporated by reference in its entirety.

FIELD OF THE INVENTION

The present invention relates to a ligand specific for annexin 2, and also to the diagnostic and therapeutic use thereof, or to the use thereof for the in vitro detection of annexin 2 in a biological sample.

TECHNICAL BACKGROUND

Annexin 2, also known as annexin A2, annexin II, lipocortin II, galpactin I heavy chain, chromobindin-8, p36 or placental anticoagulant protein IV, is a 38 kDa protein which is part of the annexin family. Annexins are proteins which have a dual cell location: cytosolic and membrane. It is encoded in humans by the ANXA2 gene. Annexin 2 is structured as 2 domains: the core which contains the $Ca^{2+}$-binding sites responsible for binding to membranes, and the N-terminal domain which has the site for binding to the S100A10 protein with which it forms a tetramer.

Annexin 2 is involved in numerous functions: angiogenesis, the metastatic process, cholesterol transport, infection by certain viruses, exocytosis and endocytosis phenomena, regulation of the action of plasminogen, fibrinolysis, ion channel formation, membrane-cytoskeleton interactions, intercellular junction formation (for a review, see Hajjar, K. A. & S. Krishnan (1999) *Trends in Cardiovascular Medicine* 9(5): 128-138).

From a pathological point of view, the overexpression of annexin A2 has been found in several human cancers, including, but not restricted to, high-grade glioma, acute promyelocytic leukemia, colorectal cancer, pancreatic cancer, renal deli carcinomas, hepatocellular carcinomas, squamous cell carcinomas, prostate cancer and lung cancer. The overexpression of annexin 2 has, moreover, been correlated with poor prognosis in colorectal cancer (Emoto et al. (2001). *Cancer* 92: 1419-26) and with a risk of recurrence after surgery in patients suffering from pancreatic cancer (Takano et al. (2008). *Ann Surg Oncol* 15:3157-68).

The involvement of annexin 2 has been reported in several diseases. Thus, it appears that abnormally high levels of annexin 2 expression on acute promyelocytic leukemia cells increase the production of plasmin, which is a fibrinolytic protein, thereby contributing to the hemorrhagic complications observed in this leukemia (Menell et al. (1.999) *New England Journal of Medicine* 340: 994-1004; Hajjar & Krishnan (1999) *Trends Cardiovasc. Med.* 9: 128-138 Stein et al. (2009) *Best Pract. Res. Clin. Haematol.* 22: 153-63).

It has also been reported that annexin 2 appears to promote angiogenesis, tumor progression and also metastases of certain cancers (Yusuke, S. et al. (2008) *Journal of Cellular Biochemistry* 105(2): 370-380).

Moreover, annexin 2 also appears to be involved in the increased risk of arterial and venous thrombosis run by patients bearing antiphospholipid antibodies (APLAs) (Zhang & McCrae (2005) *Blood* 105: 1964-1969). Annexin 2 also appears to promote the infection of cells by certain viruses.

Annexin 2 is therefore a promising therapeutic target and also an interesting diagnostic marker, and is would be advantageous to have ligands specific for this protein, whether in order to block its pathological functions or to detect it.

In this respect, it has been shown that several, protein ligands of annexin 2 have a therapeutic action. Thus, it has been shown in mice that a monoclonal antibody directed against annexin 2 makes it possible to reduce tumor growth by 70% in a murine model of Lewis lung carcinoma. (Sharma et al. (2006) *Exp. Mol. Pathol.* 81: 136-145). Similarly, it has been demonstrated that the anti-angiogenic effect of the TM601 polypeptide, a synthetic form of chlorotoxin, appears to be linked to its interaction with annexin 2 (Kesavan et al. (2010) *J. Biol. Chem.* 285: 4366-4374; Lima et al. (2010). J Cell Physiol 225: 855-864). Moreover, it has been shown that the Fab fragment of an anti-annexin 2 monoclonal antibody blocks the endothelial activation caused by APLAs (Zhang & McCrae (2005) *Blood* 105: 1964-1969).

However, the annexin 2 ligands identified to date have limitations, in particular in terms of synthesis cost, immunogenicity or affinity for their target.

SUMMARY OF THE INVENTION

The present invention follows from the unexpected identification, by the inventors, of an aptamer, of nucleotide nature, which specifically recognizes annexin 2 at the cell surface, with a dissociation constant of nanomolar order.

Thus, the present invention relates to an aptamer comprising a nucleic acid capable of specifically recognizing annexin 2 at the surface of a cell.

More particularly, the invention relates to an aptamer comprising, or consisting of, a nucleic acid comprising, or consisting of:
the sequence GGAACGCAAGAACUGAGGC-CAUGAGGCGCCUUCCCUUGC-UCAGGACGC (SEQ ID NO: 1), or
the sequence AGCUAGGCCGCAAGGUGCCU-CAACGCCAUCUGAGUGCCG-ACCCGAUCGC (SEQ ID NO: 2), or
a sequence comprising, or consisting of, at least 15 consecutive nucleotides of a polynucleotide having at least 60% identity with SEQ ID NO: 1 or SEQ ID NO: 2, with the proviso that a nucleic acid consisting of this sequence binds to annexin 2.

In one particular embodiment, the invention relates to the aptamer according to the invention, for use thereof as a medicament or a diagnostic agent.

The present invention also relates to a pharmaceutical or diagnostic composition comprising, as active substance, at least one aptamer according to the invention, in association with at least one pharmaceutically acceptable vehicle.

In this respect, the invention also relates to an in vitro method for the diagnosis of a cancer in an individual, comprising the following steps:
bringing the biological sample into contact with an aptamer according to the invention;
determining the amount of aptamer bound in the sample;
optionally, comparing the amount of aptamer bound in the sample with at least one predetermined value;
deducing therefrom whether the individual is suffering from a cancer.

The present invention also relates to a method for the diagnosis of a cancer in an individual, comprising the following steps:

administering an aptamer according to the invention to the individual;
detecting, quantifying and/or localizing the aptamer in the individual or a part of the individual;
deducing therefrom whether the individual is suffering from a cancer.

The present invention also relates to the in vitro use of an aptamer according to the invention, for detecting the presence of annexin 2, or determining the amount of annexin 2 present in a biological sample.

The present invention relates to an in vitro method for detecting or determining the amount of annexin 2 in a biological sample, comprising the following steps:

bringing the biological sample into contact with an aptamer according to the invention;
quantifying or detecting the presence or absence of aptamer bound in the sample;
deducing therefrom the amount, or the presence or absence, of annexin 2 in the sample.

The present invention also relates to a method for detecting, quantifying or localizing annexin 2, in an individual or a part of an individual, comprising the following steps:

administering an aptamer or a diagnostic composition as defined above, to the individual;
detecting, quantifying and/or localizing the aptamer in the individual or a part of she individual;
deducing therefrom the presence or absence, the amount, and/or the localization of annexin 2 in the individual or the part of the individual.

The present invention also relates to the use of an aptamer as defined above, for screening for annexin 2 ligands.

The present invention also relates to a method for screening for annexin 2 ligands, comprising the following steps:

bringing together annexin 2 and, concomitantly or successively, a ligand to be screened and an aptamer as defined above;
determining the amount of aptamer bound to annexin 2;
deducing therefrom whether the ligand is an annexin 2 ligand.

DETAILED DESCRIPTION OF THE INVENTION

As it is intended herein, an "aptamer" denotes a compound, comprising at least one nucleic acid, which is capable of binding specifically to a target, in particular of protein nature, by means of the nucleic acid. An aptamer is said to bind specifically to a target when it exhibits essentially no affinity for a compound that is structurally unrelated to the target. Preferably, in the case of a protein target, a protein compound is said to be structurally unrelated to the target according to the invention when the sequence identity between the target and the compound is less than 60%, preferably less than 70% and more preferably less than 80%. Preferably, according to the invention, an aptamer is said to exhibit essentially no affinity for a compound according to the invention in particular when the dissociation constant of the aptamer with respect to the compound is greater than $10^{-6}$ mol/l and preferably greater than $10^{-7}$ mol/l. The dissociation constant can in particular be determined, under standard conditions, using the Scatchard and Lineweaver Burk representations well known to those skilled in the art.

Advantageously, the aptamer according to the invention is specific for annexin 2, in particular human annexin 2, especially when the annexin 2 is expressed at the surface of a cell. Annexin 2, also known as annexin A2, annexin II, lipocortin II, calpactin I heavy chain, chromobindin-8, p36 or placental anticoagulant protein IV, is well known to those skilled in the art. Human annexin 2 is in particular described under the reference AAH52567.1 in the GenBank database. By way of example, human annexin 2 is represented by the sequence SEQ ID NO: 5.

The aptamer according to the invention can also comprise at least one additional group in addition to the nucleic acid. Thus, the nucleic acid according to the invention can be linked to at least one additional group. Moreover, preferentially, the aptamer according to the invention consists of the nucleic acid according to the invention and of at least one additional group according to the invention.

The additional group according to the invention can be of any type and of any nature. The additional group according to the invention can thus be a radioisotope, an organic molecule comprising 100 carbon atoms at most, a nanoparticle, in particular a micelle, a protein, in particular a glycoprotein, a carbohydrate, a lipid, or else a polynucleotide. According to the invention, it is, however, preferred that the additional group according to the invention be selected from the group consisting of a detectable label, a pharmacological compound, and a compound capable of modifying the pharmacokinetic characteristics of a nucleic acid to which it is linked, such as polyethylene glycol (PEG).

The detectable label according to the invention may be of any type; it may in particular be a fluorophore, for example fluorescein or luciferase; a radioisotope, in particular suitable for scintigraphy, for example $^{99m}$Tc; an antibody-recognizable tag, for example the c-Myc protein; an affinity tag, for example biotin; or an enzyme, for example horseradish peroxydase.

The pharmacological compound according to the invention can also be of any type; it can in particular be an anticancer chemotherapy agent, such as a cytostatic or cytolytic agent. The pharmacological compound according to the invention can also be of any nature; it can in particular be a platinum derivative, an organic molecule comprising less than 100 carbon atoms, a peptide, a nucleotide analog, a toxin, an interfering RNA, or an antisense oligonucleotide.

Preferably, the nucleic acid according to the invention is RNA. As will be clearly apparent to those skilled in the art, it is quite particularly preferred for the nucleic acid according to the invention to be single-stranded. It is also quite particularly preferred for the nucleic acid according to the invention to have a three-dimensional structure which enables it to bind specifically to annexin 2. Moreover, the backbone or the ribose of the nucleic acid according to the invention can be totally or partially modified, in particular to make is resistant to hydrolytic degradation, in particular due to the action of nuclease, especially when the nucleic acid is RNA. Such modifications are well known to those skilled in the art and cover in particular modifications of the OH function on the carbon in the 2' position of the ribose by methylation, or the substitution of this OH function with an amino group or with a halogen, in particular with fluorine, and also recourse to a phosphorothioate backbone, or to structures of locked nucleic acid (DNA) or peptide nucleic acid (PNA) type. Thus, preferably, the nucleic acid according to the invention is an RNA in which the riboses of the pyrimidine nucleotides bear a fluorine atom on the carbon in the 2' position, it being possible for the riboses of the purine nucleotides to be unchanged.

A sequence having at least 60% nucleotide identity with SEQ ID NO: 1 or SEQ ID NO: 2 according to the invention differs in particular from SEQ ID NO: 1 or 2 via the insertion, the deletion or the substitution of at least one nucleotide. As it is intended herein, the percentage of identity between two sequences is defined as the number of positions for which the bases are identical when the sequences are optimally aligned, divided by the total number of bases of the longer of the two sequences. Two sequences are said to be optimally aligned when the percentage of identity is at a maximum. Moreover, as will become clearly apparent to those skilled in the art, it may be necessary to make use of additions of gaps so as to obtain optimal alignment between the two sequences.

A nucleic acid is said to bind to annexin 2 if the dissociation constant of the nucleic acid with respect to annexin 2, in particular human annexin 2, preferably expressed by a cell, in particular a cell of the CHO, HEK293, MDA MB 231, MCF-7, A431, PC12 MEN2A, U87, 4T1 or EMT6 cell line, as is illustrated in the examples, is less than $10^{-6}$ mol/l and preferably less than $10^{-7}$ mol/l.

As will be clearly apparent to those skilled in the art, when the aptamer according to the invention comprises a nucleic acid according to the invention, it can also comprise other nucleic acids. On the other hand, when the aptamer according to the invention consists of the nucleic acid according so she invention, it does not comprise other nucleic acids. Similarly, when the nucleic acid according to the invention comprises a sequence, it can also comprise additional sequences extending from the 5' and/or 3' end of the sequence in question. On the other hand, when the nucleic acid according to the invention consists of a sequence, it does not comprise additional sequences in addition to the sequence in question.

A sequence comprising SEQ ID NO: 1 or 2 according to the invention can in particular comprise sequences on the 5' and/or 3' end aimed at structuring the nucleic acid. It is thus preferred for the nucleic acid according to the invention to comprise, or to consist of, SEQ ID NO: 3 or 4, which respectively comprise SEQ ID NO: 1 and 2. In this context, the invention then also relates, in particular, to a nucleic acid comprising, or consisting of, at least 15 consecutive nucleotides of a sequence having at least 60% identity with SEQ ID NO: 3 or SEQ ID NO: 4, with the proviso that a nucleic acid consisting of this sequence binds to annexin 2.

Preferably, the sequence comprising, or consisting of, at least 15 consecutive nucleotides of a sequence having at least 60% identity with SEQ ID NO: 1, 2, 3 or 4 according to the invention, comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 60% identity with SEQ ID NO: 1, 2, 3 or 4.

Preferably also, the sequence comprising, or consisting of, at least 15 consecutive nucleotides of a sequence having at least 60% identity with SEQ ID NO: 1, 2, 3 or 4 according to the invention, comprises or consists of at least 15 consecutive nucleotides of a sequence having at least 65%, 70%, 75%, 80%, 85%, 90%, 95% or 100% identity with SEQ ID NO: 1, 2, 3 or 4 according to the invention.

More preferably, the sequence comprising, or consisting of, at least 15 consecutive nucleotides of a sequence having at least 60% identity with SEQ ID NO: 1, 2, 3 or 4 according to the invention, comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 80% identity with SEQ ID NO: 1, 2, 3 or 4.

More preferably still, the sequence comprising, or consisting of, at least 15 consecutive nucleotides of a sequence having at least 60% identity with SEQ ID NO: 1, 2, 3 or 4 according to the invention, comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 85% identity with SEQ ID NO: 1, 2, 3 or 4.

Even more preferably, the sequence comprising, or consisting of, at least 15 consecutive nucleotides of a sequence having at least 60% identity with SEQ ID NO: 1, 2, 3 or 4 according to the invention, comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 90% identity with SEQ ID NO: 1, 2, 3 or 4.

Particularly preferably, the sequence comprising, or consisting of, at least 15 consecutive nucleotides of a sequence having at least 60% identity with SEQ ID NO: 1, 2, 3 or 4 according to the invention, comprises or consists of at least 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 consecutive nucleotides, or all the consecutive nucleotides, of a sequence having at least 95% identity with SEQ ID NO: 1, 2, 3 or 4.

Moreover, alternatively, the sequence comprising, or consisting of, at least 15 consecutive nucleotides of a sequence having at least 60% identity with SEQ ID NO: 1, 2, 3 or 4 according to the invention can consist of a sequence of 95 nucleotides having at least 60%, 65%, 70%, 75%, 80%, 85%, 90% or 95% identity with SEQ ID NO: 3, and a nucleic acid consisting of this sequence is capable of adopting the structure of formula (I) below:

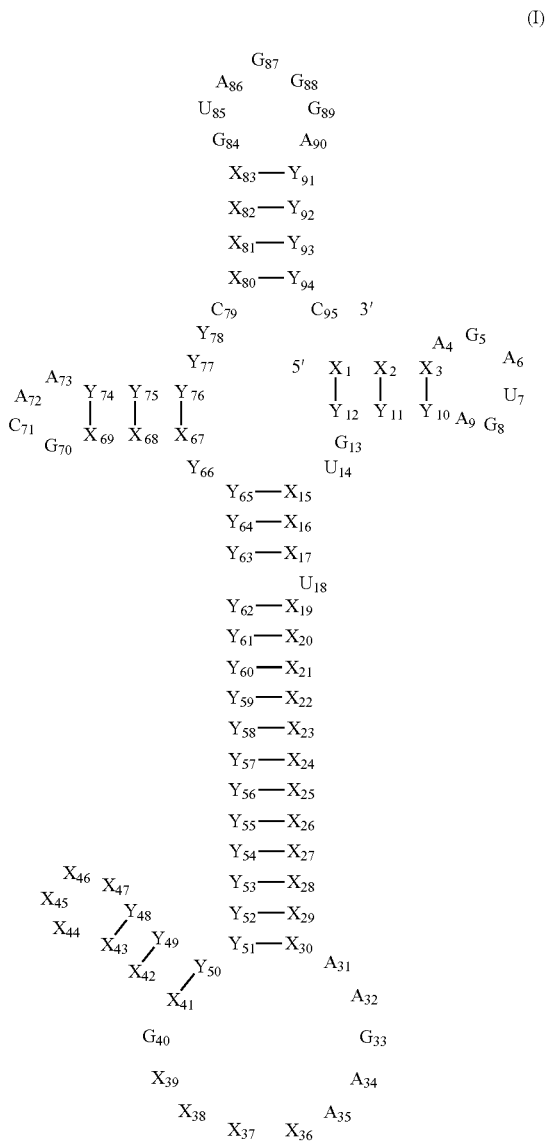

in which:
A, C, G and U are the ribonucleotides adenosine, cytidine, guanosine and uridine;
each X and Y, which may be identical or different, represents A, C, G or U;

each of the pairs X-Y or Y-X, which may be identical or different, represent A-U, U-A, G-C, C-G, G-U or U-G pairs;

preferably, (i) $X_{36}, X_{37}; X_{38}$ and $X_{39}$ are capable of forming A-U, U-A, G-C, C-G, G-U or U-G pairs, respectively, with $Y_{66}, Y_{65}, Y_{64}$ and $Y_{63}$, and (ii) $X_{44}, X_{45}, X_{46}$ and $X_{47}$ are capable of forming pairs, respectively, with $Y_{78}, Y_{77}, Y_{76}$ and $Y_{75}$.

Alternatively also, the sequence comprising, or consisting of, at least 15 consecutive nucleotides of a sequence having at least 60% identity with SEQ ID NO: 1, 2, 3 or 4 according to the invention can consist of a sequence of 96 nucleotides having at least 60%, 65%, 70%, 75%, 80%, 85%, 90% or 95% identity with SEQ ID NO: 4, and a nucleic acid consisting of this sequence is capable of adopting the structure of formula (II) below:

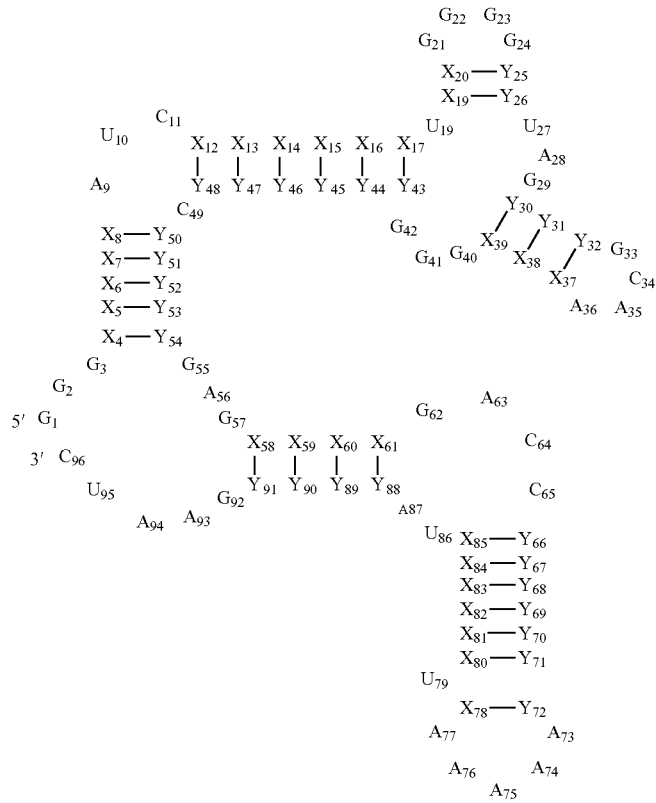

(II)

in which:
   A, C, G and U are the ribonucleotides adenosine, cytidine, guanosine and uridine;
   each X and Y, which may be identical or different, represents A, C, G or U;
   each of the pairs X-Y or Y-X, which may be identical or different, represent A-U, U-A, G-C, C-G, G-U or U-G pairs.

Those skilled in the art can easily determine the secondary structure capable of being adopted by a nucleic acid having a sequence according to the invention, for example using modeling algorithms or software well known to those skilled in the art, such as mfold (version 3.4) described in *Nucleic Acids Res.* (2003) 31: 3406-15 and *vsfold5 RNA Pseudoknot Prediction* described in *PLoS One* (2007) 2: 905. In this respect, the inventors have established, using such modeling tools, that the ACE8 aptamer of sequence SEQ ID NO: 3, which is described in the examples, adopts a structure of formula (I) and that the ER4 aptamer, of sequence SEQ ID NO: 4, which is described in the examples, adopts a structure of formula (II).

When the aptamer according so the invention is used as a medicament or is included in a pharmaceutical composition, it is in particular used for preventing or treating cancers, especially by inhibiting angiogenesis, for preventing or treating diseases involving ocular neovascularization, such as age-related macular degeneration and diabetic retinopathy, for preventing or treating arterial or venous thrombosis in patients bearing antiphospholipid antibodies (APLAs), for preventing or treating hemorrhages in patients suffering from acute promyelocytic leukemia, and also for preventing or treating viral infections.

When the aptamer according to the invention is used as a diagnostic agent or is included in a diagnostic composition, it is in particular used for diagnosing cancers.

Preferably, in the methods for detection or for diagnosis according to the invention, the detection of aptamer bound in the sample is carried out by performing a polymerase chain reaction (PCR) intended to amplify the aptamer. Preferably, when the nucleic acid according to the invention comprises SEQ ID NO: 3 or 4, the PCR is performed using the pair of primers of sequences GATTCTGCCTACGAACGAC-GACTT (SEQ ID NO: 6) and GGGAGATGATCCGTTGAT-GCGAG (SEQ ID NO: 7). Moreover, the invention also relates to a nucleic acid comprising or consisting of SEQ ID NO: 6 or SEQ ID NO: 7. Preferably also, in the methods for detection or for diagnosis according to the invention, when the aptamer is administered to an individual, the aptamer is preferably detectable by means of in vivo imaging methods, which are in particular external, such as planar or three-dimensional (3D) fluorescent imaging, or internal, such as endoscopy, for example.

DESCRIPTION OF THE FIGURES

FIG. 1: Selection Protocol Diagram

FIG. 1 represents the aptamer selection protocol used by the inventors for obtaining the ACE8 aptamer.

FIGS. 2 and 3: Effect of Endothelin on Aptamer Binding

FIG. 2 represents the binding of the ACE8, ER2 and ER4 aptamers on CHO-ET$_B$R cells (top graph) and untransformed CHO cells (CHO-WT, bottom graph) in the presence or absence of endothelin. The CHO-ET$_B$R cells were preincubated in wells for 30 minutes (dark columns) or not preincubated (light columns) with 100 nM of endothelin. The radiolabeled aptamers are then added at a concentration of 10 nM for 30 minutes. After several washes, the radioactivity bound to the cells is counted and the amount of aptamers bound is determined (in pmol/well).

FIG. 3 makes it possible to visualize the endothelin on CHO-ETBR and CHO-WT. The cells are incubated for 30 min with endothelin-1-FAM at a concentration of 20 nM. After two washes, the cells are visualized by fluorescent microscopy (top photographs) and show strong internalization of the endothelin. The bottom photographs represent the bright fields corresponding to the fluorescent fields.

FIG. 4 represents the secondary structure of the ACE8 aptamer predicted using the mfold program (version 3.2, http://mfold/bioinfo/rpi.edu/cgi-bin/rna-form1.cgi). On this structure, the fixed sequences enabling PCR amplification have been highlighted in gray. The potential formation of pseudoknots predicted by the Vsfold5 program has been added (Vsfold5 pseudoknot prediction program, http://www.rna.it-chiba.ac.jp/~vsfold/vsfold5/).

FIG. 5 represents photographs taken by fluorescence microscopy (top photographs) and the corresponding bright fields (bottom photographs) for A-431, HEK-293, MCF-7, MDA-MB-231 and PC12 MEN2A cells brought into contact with the ACE8 aptamer or the control sequence labeled with phycoerythrin. The aptamer or the control sequence is incubated on the cells for 15 min at a concentration of 50 nM. After 2 washes, the cells are visualized under a fluorescence microscope. The exposure time was set at 200 ms for all the experiments.

FIG. 6 represents photographs taken by fluorescence microscopy of MCF-7 cells incubated in the presence of the ACE8 aptamer or of a control sequence coupled to phycoerythrin and in the presence of proteinase K (+PK), of trypsin (+T) or of PBS. Briefly, the MCF-7 cells are detached with a solution of PBS-5 mM EDTA. The cells in suspension are preincubated with proteinase K (+PK), trypsin (+T) or PBS for 10 min at 37° C. 1 ml of inactivated fetal calf serum (iFCS) is added in order to inhibit the enzymes. The cells are then incubated for 30 min with the ACE8 aptamer or the control sequence coupled to phycoerythrin and washed twice. The cells are observed between slide and cover slip under an epifluorescence microscope.

FIG. 7 represents the bright fields corresponding to the fluorescent fields.

FIG. 8 represents the protocol for identifying the target of the ACE8 aptamer. Briefly, the biotinylated aptamer is incubated on the MCF-7 cells in suspension. After several washes, streptavidin-coupled magnetic beads are added. Only the cells which have bound the biotinylated ACE8 aptamer will be retained on the beads. The cells are then lysed and the proteins retained by the ACE8 aptamer are eluted. The proteins are then loaded onto an SOS-PAGE gel and the specific bands are analyzed by mass spectrometry.

FIG. 9 shows a photograph of an SDS-PAGE gel on which the eluates originating from beads placed directly in contact with the cells (beads), a control oligonucleotide (Ctrl), or the ACE8 aptamer, are migrated. The main bands corresponding no the eluate originating from the aptamer are indicated. The band corresponding to bovine serum albumin (BSA), used as a nonspecific competitor, is also represented. Briefly, the proteins are loaded onto an SDS 10% PAGE gel. The gel is then stained using the proteosilver silver stain kit (sigma). The interesting bands are cut out, destained with the same kit and analyzed by mass spectrometry.

FIG. 10 represents the amount of mRNA encoding annexin 2 (y-axis, as percentage of the amount expressed in the absence of siRNA) expressed by MCF-7 cells in the presence of an siRNA which targets (+siRNA) or does not target (−siRNA) the annexin 2 mRNA. The cells are optionally transfected with an siRNA which targets annexin 2, in the presence of lipofectamine. 72 h later, total RNA of the MCF-7 cells is extracted and reverse-transcribed, and a qPCR is carried out using primers specific for annexin 2 and for the P0 gene in order to standardize the results.

FIG. 11 represents the amount of ACE8 aptamers (y-axis, as percentage of the amount be in the absence of siRNA) bound to the surface of MCF-7 cells in the presence of an siRNA which targets (Annexin 2 siRNA) or does not target (control siRNA) the annexin 2 mRNA. The MCF-7 cells are transfected with an siRNA targeting annexin 2 or with a control siRNA, in the presence of lipofectamine. 72 h later, the radiolabeled ACE8 aptamer or a radiolabeled control sequence is incubated at a concentration of 10 nM for 15 min. The radioactivity is then counted. ** corresponds to a significant difference in the binding of ACE8 between the cells transfected with the siRNA targeting annexin and the cells transfected with the control siRNA, measured by means of a student's test with P<0.01.

FIG. 12 represents fluorescence microscopy photographs of the ACM aptamer or of a control sequence, coupled directly to Alexa Ulysis 546, or indirectly to Alexa Fluor 546 maleimide, by having previously coupled them to an SH group, or to phycoerythrin and to Quantum. Dots, by having previously coupled them to a biotin, and placed in the presence of MCF-7 cells. The labeled aptamers are incubated for 15 min at a concentration of 50 nM on the MCF-7 cells. After 2 washes, the cells are observed under a fluorescence microscope.

FIG. 13 represents fluorescence microscopy photographs of MCF-7 cells placed in the presence of the ACE8 aptamer or of a control sequence, coupled to Quantum. Dots (QDs) for 15 min or 1 h. The aptamer enables rapid targeting of the QDs to the membrane of the MCF-7 cells, and then a part, is internalized in less than one hour. A control sequence coupled to QDs shows no labeling of the cells.

MCF-7 or A431 cells are incubated with the ACE8 aptamer or the control sequence which are labeled with phycoerythrin at a concentration of 5 nM for 30 min. The cells are then washed and analyzed by flow cytometry. FIG. 14 represents the amount of MCF-7 (left-hand graph) and A431 (right-hand graph) cells sorted (y-axis) as a function of the fluorescence emitted by the ACE8 aptamer or the control sequence (x-axis, arbitrary units).

The ACE8 aptamer or a control sequence, which are labeled with AlexaFluor 680, were injected into mice developing tumors following a subcutaneous injection of MCF-7 cells. FIG. 15 represents their biodistribution measured using photographs obtained at various times by planar fluorescent imaging using a TomoFluo3D instrument developed by CEA-LETI. The tumor and also the reference zone which makes it possible to measure the signal in the tumor/internal reference ratio are indicated by white arrows.

The ACE8 aptamer or a control sequence, labeled with AlexaFluor680, were injected into mice developing tumors following a subcutaneous injection of MCF-7 cells. Three hours post-injection, the fluorescent signal in the tumor was measured by fluorescent tomography using a TomoFluo3D instrument developed by CEA-LETI. FIG. 16 shows a 3D rendering of the fluorescence at the level of the tumor in the cube above a planar fluorescence image of the animal. FIG. 17 represents the amount of fluorescence determined in triplicate as a percentage of the dose injected (% DI, y-axis) in the tumor for the ACE8 aptamer and a control sequence. The symbol * corresponds to a significant difference in the ratio between ACE8 and the control sequence measured by means of a student's test with P<0.05.

Human umbilical vein endothelial cells (HUVECs) were cultured, with or without oligonucleotide (5 µM), on Matrigel in a medium with a low growth hormone content containing 2% (v/v) of fetal calf serum and basic fibroblast growth factor (bFGF at 3 ng/ml). Under these conditions, the HUVECs form a network of endothelial tubes which can be observed by microscopy and represents a proven in vitro model of angiogenesis. FIG. 18 represents microscopy photographs of the networks formed in the absence of oligonucleotide, in the presence of a control sequence, and in the presence of the ACE8 aptamer. The formation of this network is not affected by the presence of the control sequence. On the other hand, the ACE8 aptamer strongly inhibits the formation of this network. FIG. 19 represents the number of tubes per node of cells on four randomly chosen fields of view, in the absence of oligonucleotide (control), in the presence of a control sequence, and in the presence of the ACE8 aptamer. *** corresponds to a significant difference in the ratio between ACE8 and the control sequence measured by means of a student's test with P<0.001.

Each radiolabeled aptamer is incubated at a concentration of 10 nM on CHO-$ET_BR$ cells in the presence (dark columns) or absence (light columns) of the other two nonradiolabeled aptamers in excess (100 nM) for 30 minutes. After several washes, the radioactivity bound to the cells is counted and the amount of aptamers bound is determined (in pmol/well). FIG. 20 represents the binding (y-axis, in pmol/well) of the ACE8, ER2 or ER4 aptamer, alone (first column) or in the presence of the other two (second column). This experiment demonstrates competition between ACE8 and ER4 for binding to the cells, suggesting that ER4 binds to annexin 2.

FIG. 21 represents the secondary structure of the ER4 aptamer predicted using the mfold program (version 3.2, http://mfold.bioinfo.rpi.edu/cgi-bin/rna-form1.cgi).

FIG. 22 shows a greater capture of the ACE8 aptamer on the annexin 2/S100A10 heterotetramer compared with the control sequence. FIG. 23 represents the quantification of the amount of oligonucleotides retained on the filter as a function of the concentration of annexin 2/S100A10 heterotetramer.

EXAMPLES

Example 1

Figure 4:
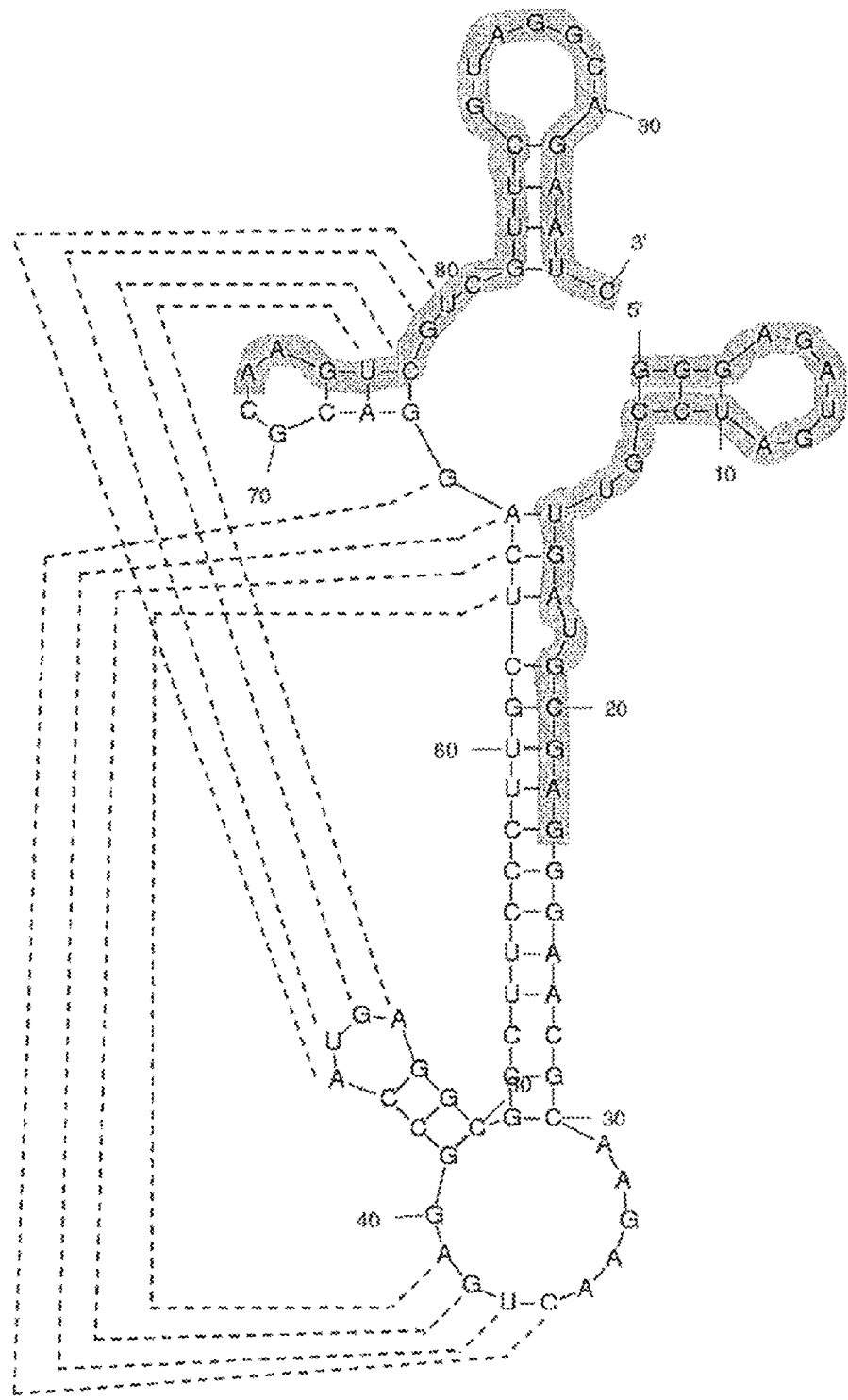
FIG. 4: ACE8 Aptamer Structure Prediction

Obtaining the ACE8 Aptamer Specific for Annexin 2

1. Distribution of the ACE8 Aptamer after 15 and 18 Rounds of Selection on CHO-ETBR Cells The inventors used the SELEX technique, in particular described in application WO 2005/093097, for the purpose of selecting aptamers against she endothelin type B receptor ($ET_BR$). For this, CHO cells stably overexpressing $ET_BR$ were used for the selection and CHO cells not expressing $ET_BR$ were used for the counterselection (FIG. 1).

During this SELEX, the inventors modified various parameters for the purpose of gradually increasing the selection pressure (Table 2). Compared with the protocol described in application WO 2005/093097, the inventors introduced a few modifications: during a few rounds, the selection and counterselection steps were inverted (rounds 14 and 15) and the aptamers were detached from the cells by adding endothelin-1 for the last three rounds (16 to 18). The selection conditions are given in Table 1 below:

TABLE 1

Evolution of selection pressure during the SELEX

| Cycle NO | Number of cells for the selection (million) | Number of cells for the counter-selection (million) | Selection-counter-selection inversion | Incubation volume (ml) | 2'F-Py-RNA concentration (μM) | Incubation time (minutes) | Number of washes | Specific washing condition | Competitor added during incubation (100 μg/ml of tRNA) | Elution mode |
|---|---|---|---|---|---|---|---|---|---|---|
| 1 | 10 | 10 | | 3 | 1 | 30 | 2 | | | tri-reagent |
| 2 | 10 | 10 | | 3 | 1 | 30 | 3 | | | tri-reagent |
| 3 | 10 | 10 | | 3 | 1 | 25 | 3 | | | tri-reagent |
| 4 | 5 | 5 | | 3 | 1 | 25 | 3 | | | tri-reagent |
| 5 | 5 | 5 | | 3 | 1 | 25 | 4 | | | tri-reagent |
| 6 | 5 | 5 | | 3 | 1 | 20 | 4 | | | tri-reagent |
| 7 | 5 | 5 | | 3 | 0.5 | 20 | 5 | | | tri-reagent |
| 8 | 5 | 5 | | 3 | 0.5 | 15 | 5 | | | tri-reagent |
| 9 | 5 | 5 | | 3 | 0.5 | 15 | 5 | 5 min for the last wash | | tri-reagent |
| 10 | 5 | 5 | | 3 | 0.5 | 10 | 5 | 5 min for the last wash | | tri-reagent |
| 11 | 5 | 5 | | 3 | 0.5 | 10 | 5 | 5 min for the last wash | + | tri-reagent |
| 12 | 5 | 5 | | 3 | 0.5 | 10 | 5 | 5 min for the last wash | + | tri-reagent |
| 13 | 5 | 5 | | 3 | 0.5 | 10 | 5 | 5 min for the last 2 washes | + | tri-reagent |
| 14 | 5 | 5 | + | 3 | 0.5 | 10 | 5 | 5 min for the last 2 washes | + | tri-reagent |
| 15 | 5 | 5 | + | 3 | 0.5 | 10 | 5 | 5 min for the last 2 washes | + | tri-reagent |
| 16 | 5 | 5 | | 3 | 0.025 | 10 | 5 | 5 min for the last 2 washes | + | elution with 250 nM of endothelin-1 |
| 17 | 5 | 5 | | 3 | 0.025 | 10 | 5 | 5 min for the last 2 washes | + | elution with 250 nM of endothelin-1 |
| 18 | 5 | 5 | | 3 | 0.025 | 10 | 5 | 5 min for the last 2 washes | + | elution with 250 nM of endothelin-1 |

The libraries resulting from round 15 and from round 18 were cloned and sequenced. Interestingly, one sequence (ACE8) is twice as abundant in round 18 than in round 15.

2. Effect of Endothelin on the Binding of the Aptamers

The inventors tested the affinity of about thirty sequences for these cells at 25 nM. This enabled them to identify about ten particularly advantageous aptamers with strong affinity for CHO-$ET_BR$ cells. Among all these aptamers, those for which the affinity for the cells could be linked to the expression of the endothelin type B receptor were sought. For this, the inventors compared the affinity of the aptamers for CHO-$ET_BR$ cells preincubated in the presence of endothelin. When endothelin binds to the $ET_BR$ receptor, the receptor is very rapidly internalized (FIG. 3). Following the internalization of the endothelin receptor, three aptamers showed a loss of affinity for the cells (ACE8 (SEQ ID NO: 3), ER2 (SEQ ID NO: 4) and ER4 (SEQ ID NO: 8)) (FIG. 2). However, all these aptamers also have affinity for CRC-NT cells, which do not express the receptor. Furthermore, following endothelin treatment of the CHO-WTs, the affinity of these aptamers does not decrease. All these experiments appear to demonstrate that the target of these aptamers is not $ET_BR$, but another protein which could be endocytosed at the same time as $ET_BR$ after binding of endothelin.

In order to evaluate the potential value of these aptamers, the inventors measured their affinity on MCF-7 cells. These human cells derived from a breast cancer line are known to express endothelin type A and B receptors. Interestingly, the ACE8 aptamer and the ER4 aptamer showed a strong affinity for MCF-7 cells. This demonstrates that these aptamers can bind to a target of human origin and not only to the surface of hamster cells. Furthermore, binding experiments revealed that the target of the ACE8 aptamer was 10 times more abundant at the surface of MCF-7 cells than at the surface of CHO cells. Following this result, the inventors focused more particularly on the ACE8 aptamer.

3. Sequence of the ACE8 Aptamer

The sequence of the ACE8 aptamer is the following:

(SEQ ID NO: 3)
5' GGGAGAUGAUCCGUUGAUGCGAGGGAACGCAAGAACUGAGGCCAU

GAGGCGCCUUCCCUUGCUCAGGACGCAAGUCGUCGUUCGUAGGCAGAA

UC 3'.

It should be noted that, in order to improve the nuclease resistance of the ACE8 aptamer, the riboses of the pyrimidines bear a fluorine atom on the carbon in the 2' position (the riboses of the purines bear, for their part, as is the case in natural RNA, a hydroxyl function (OH) on the carbon in the 2' position).

FIG. 4 represents a prediction of the secondary structure of the ACE8 aptamer carried out using the mfold software (version 3.4) (*Nucleic Acids Res.* (2003) 31: 3406-15) and the vsfold5 RNA Psuedoknot Prediction software (*PLoS One* (2007), 2: 905).

4. Characterization of the ACE8 Aptamer a—Validation of the Use of the ACE8 Aptamer for Establishing a Profile of Expression at the Surface of Various Cell Lines The affinity and the Cmax of the ACE8 aptamer were determined for various cancer lines (Table 2).

TABLE 2

Affinity and number of targets of the ACE8 aptamer per cell for various cell lines

| Species | Line name | Kd (nM) | Cmax (pM) |
|---|---|---|---|
| Human | MCF-7 | 4.9 +/− 1.7 | 484 +/− 81 |
|  | A-431 | 5.3 +/− 1.1 | 450 +/− 35 |
|  | MDA-MB-231 | 4.4 +/− 0.6 | 167 +/− 16 |
|  | U87-MG | 12.7 +/− 4.4 | 245 +/− 55 |
|  | HEK-293 | 4.4 +/− 0.8 | 269 +/− 21 |
| Mouse | 4T1 | 3.7 +/− 0.3 | 247 +/− 11 |
|  | EMT6 | 7.5 +/− 1.3 | 261 +/− 53 |
| Hamster | CHO-ETBR | 3.4 +/− 0.8 | 86 +/− 13 |
| Rat | PC12-MEN-2A | 18.8 +/− 2.6 | 914 +/− 134 |

The binding curves were obtained for each cell type. On the basis of the specific binding, and using the Scatchard representation, the Kd and the number of targets per cell were determined for each of the cell types. The target of the ACE8 aptamer appears to be highly abundant at the surface of two human cancer lines (MCF-7 and A-431).

The ACE8 aptamer has an affinity of approximately 4 nM for most of the cell lines, except for the PC12 MEN 2A cells and the 187 cells, where the Kd exceeds about ten nM. The number of targets is very different depending on the cell, type, ranging from a Cmax of 86+/−13 pM for the CHO cells to 484+/−81 pM for the MCF-7 cells. Interestingly, the target of the ACE8 aptamer appears to be very abundant at the surface of the MCF-7 human breast cancer line and on the A-431 human epidermal carcinoma line.

b—Validation of the Use of the ACE8 Aptamer in Microscopy

Figure 5:
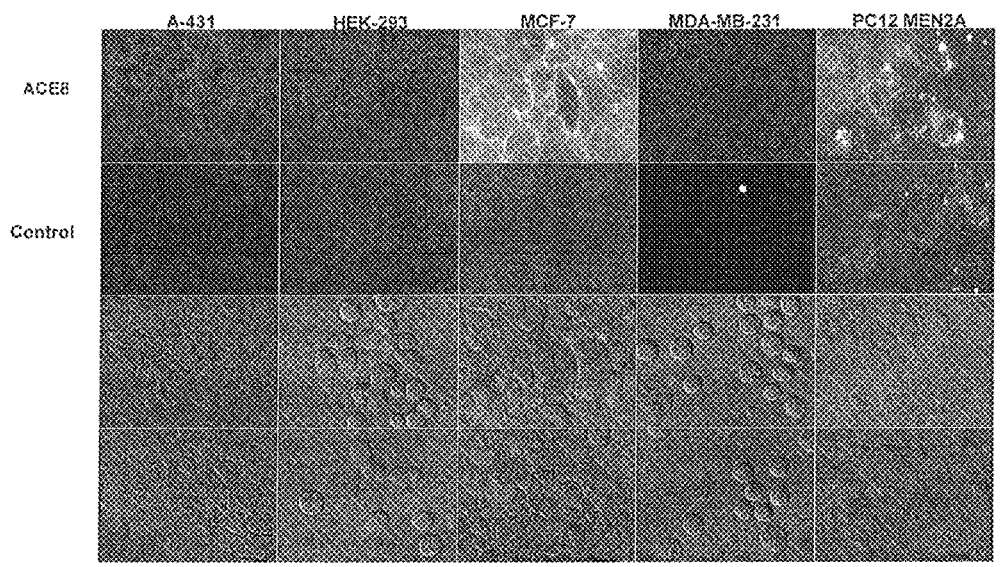
FIG. 5: Visualization of the ACE8 Aptamer on Various Cell Types

Once labeled with a fluorescent compound (phycoerythrin), the aptamer could be used in microscopy (FIG. 5). A contrast could be observed with the A-431 and MCF-7 cells, the cell types which have most targets (450+/−35 and 484+/−81 pM, respectively). Given the very high number of targets at the surface of MCF-7 cells and the good contrast observed by microscopy, the inventors chose to go more deeply into the study of the ACE8 aptamer on this cell type, which also represents the advantage of being a breast cancer line, thus indicating that the ACE8 aptamer could possibly target a protein involved in this cancer.

Figure 6:
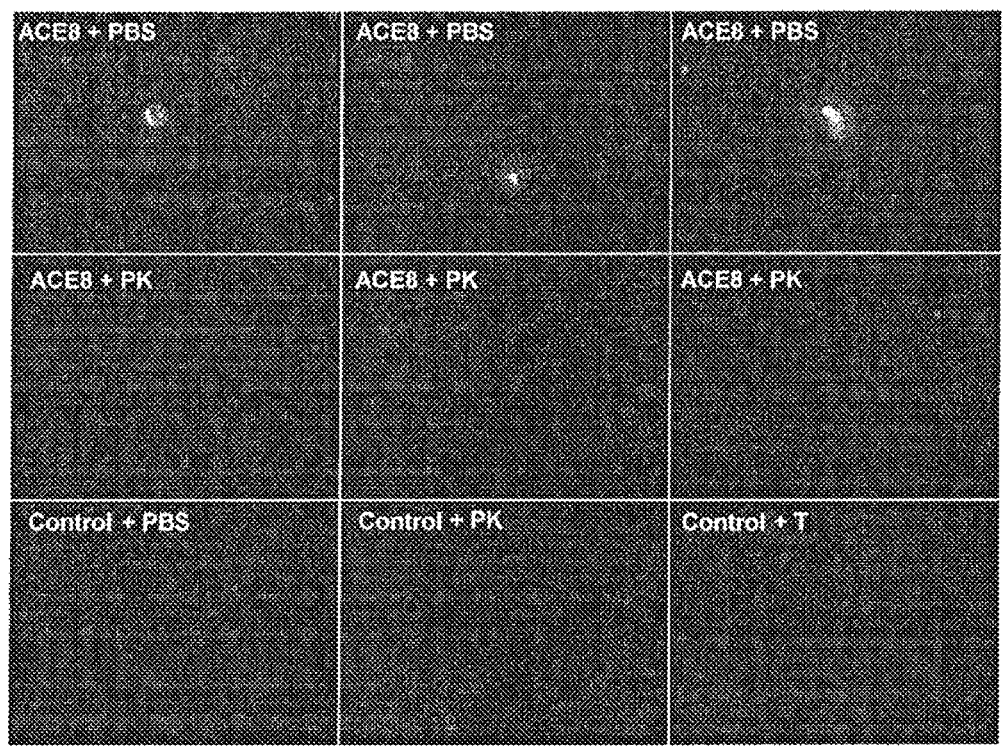
FIGS. 6 and 7: Binding of the ACE8 Aptamer on MCF-7 Cells in Suspension
Figure 7:
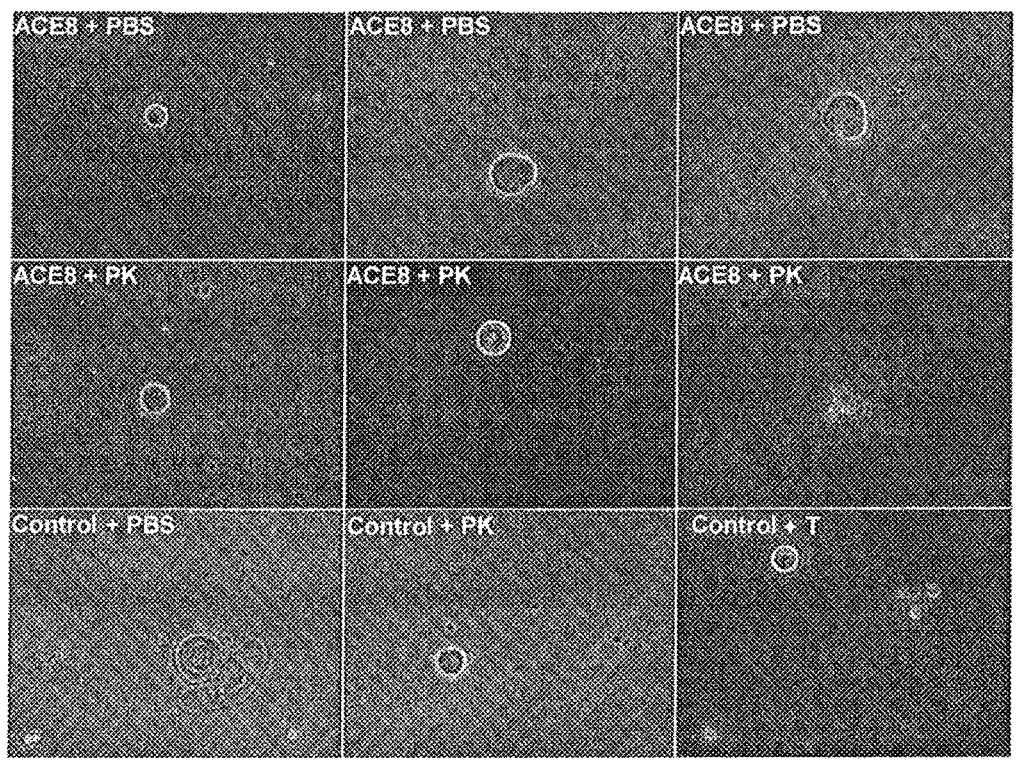

5. Identification of the Target of the ACE8 Aptamer a. Validation of the Protocol: Binding of the ACE8 Aptamer to Cells in Suspension and Determination of the Nature of the Target Before trying to purify the target of the ACE8 aptamer, the inventors first of all validated, on the one hand, that the ACE8 aptamer still binds when the cells are in suspension (FIGS. 6 and 7). On the other hand, when the cells are incubated with trypsin and proteinase K, the binding of the aptamer is lost, thereby demonstrating that the target of the aptamer is a protein.

b. Protocol for Purifying the Target of the Aptamer

In order to identify the target of the ACE8 aptamer, a protocol derived from Berezovski et al, (2008) *J. Am. Chem. Soc., Aptamer-Facilitated Biomarker Discovery* (AptaBiD) was used, in which BSA was added as a competitor in order to prevent the nonspecific binding of proteins to the beads. The protocol is summarized in FIG. 8.

c. SDS-PAGE Gel and Mass Spectrometry

Figure 8:
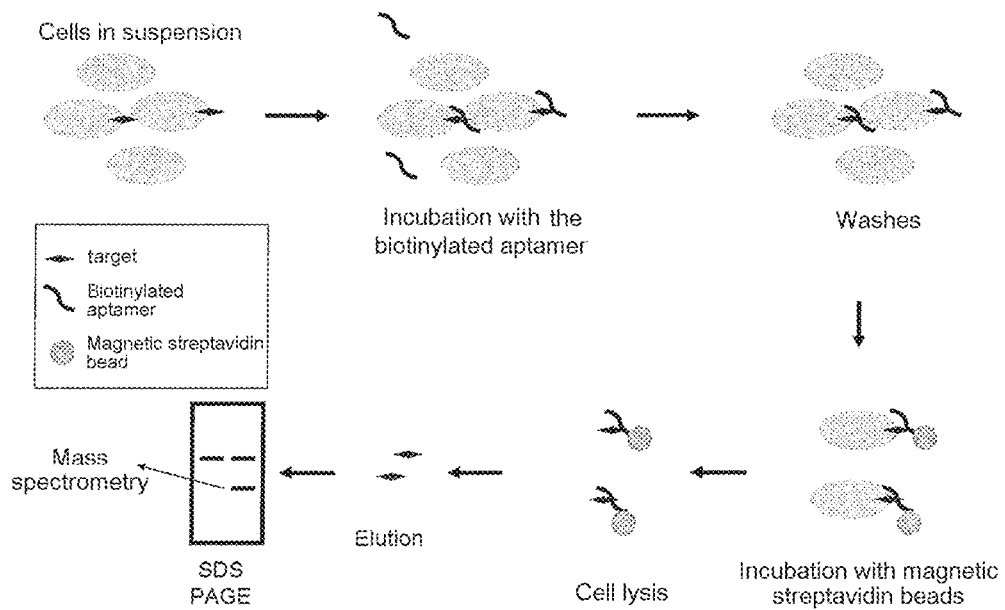
FIG. 8: Protocol for Identifying the Target of the ACE8 Aptamer
Figure 9:
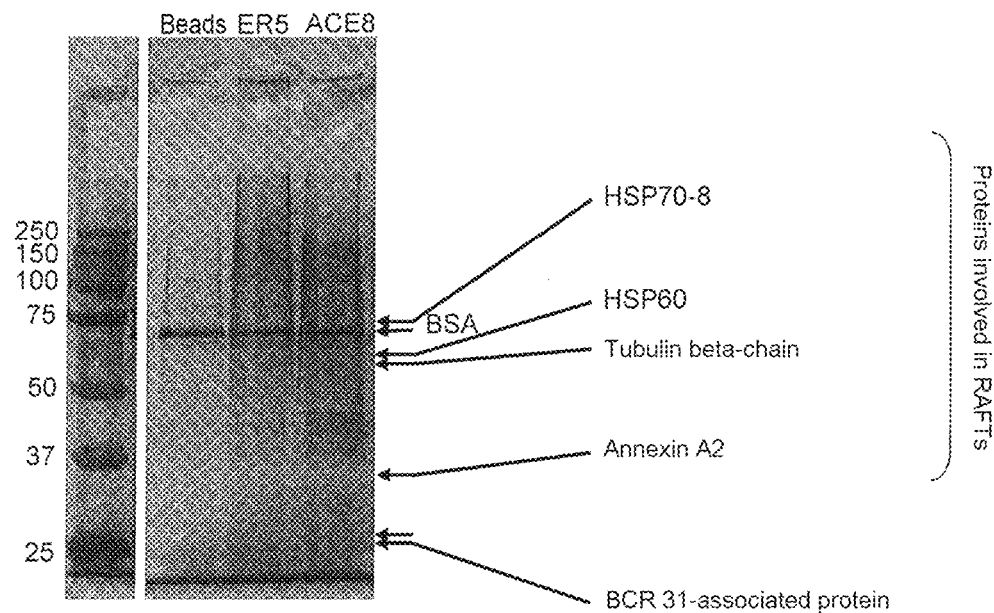
FIG. 9: Protein Migration by SDS-PAGE Electrophoresis

The proteins eluted at the end of the protocol summarized in FIG. 8 were analyzed by electrophoresis (FIG. 9). 6 bands specific for the ACE8 aptamer were identified. These bands were cut out and analyzed by mass spectrometry. Among the various proteins identified, 4 are involved in lipid RAFTs. This suggests that the target of the ACE8 aptamer is a protein located in RAFTS. Among these proteins, the inventors chose to focus more particularly on annexin 2 in view of the strength of the band for this protein.

d. Validation of the Target of the ACE8 Aptamer

Figure 10:
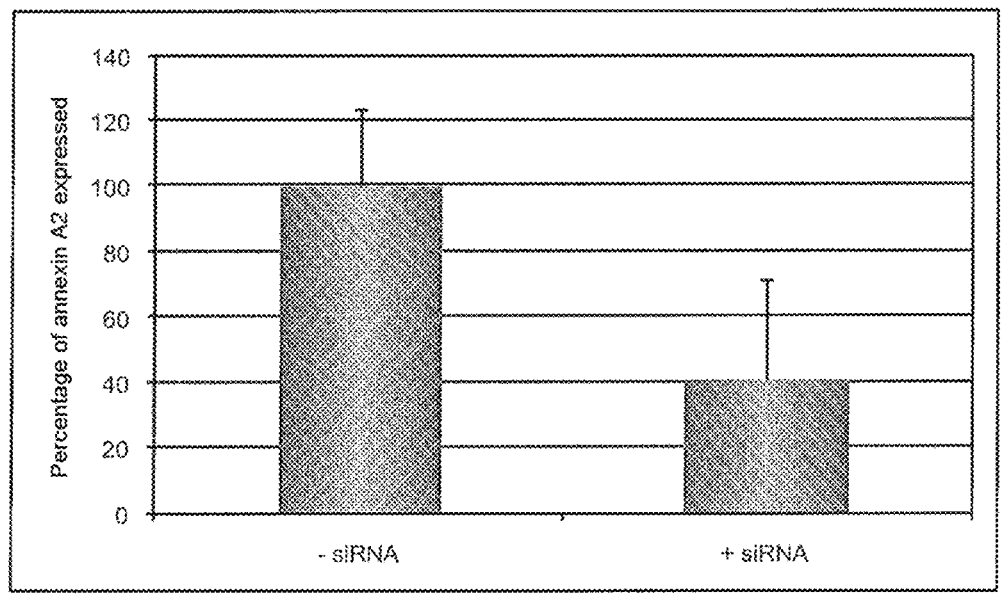
FIG. 10: Study of the Effect of siRNAs on Annexin 2 Expression by qPCR in MCF-7 Cells
Figure 11:
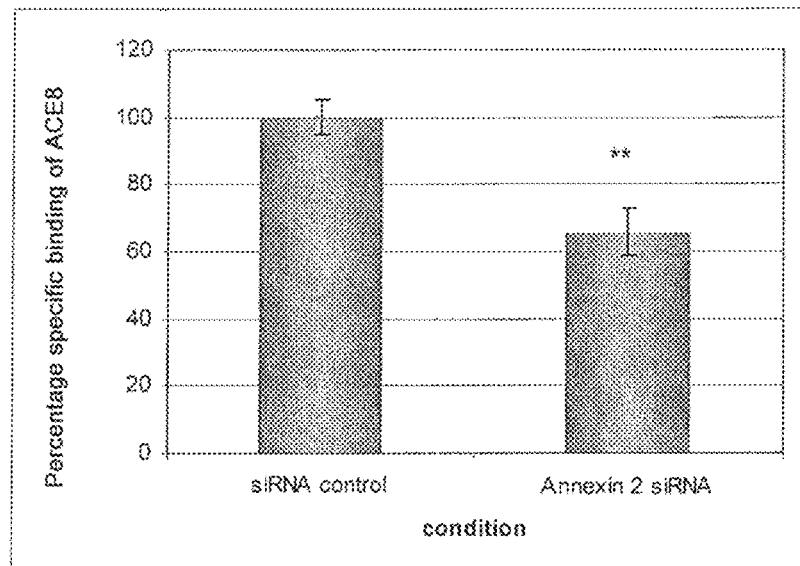
FIG. 11: Decrease in Binding of the ACE8 Aptamer after Treatment with an siRNA Targeting Annexin 2

In order to validate the target of the ACE8 aptamer, siRNA (SEQ ID NO: 9 and 10) targeting annexin 2 were used. As shown in FIG. 10, a 60% decrease in annexin 2 expression is observed 72 h after transfection of these siRNAs. Notably, when the ACE8 aptamer is incubated with cells transfected with the siRNA targeting annexin 2, the binding of the aptamer is reduced by 40% compared with MCF-7 cells transfected with a control siRNA (FIG. 11). These results indicate that the target of the ACE8 aptamer is indeed annexin 2

Example 2

Use of the ACE8 Aptamer in Microscopy

Figure 12:
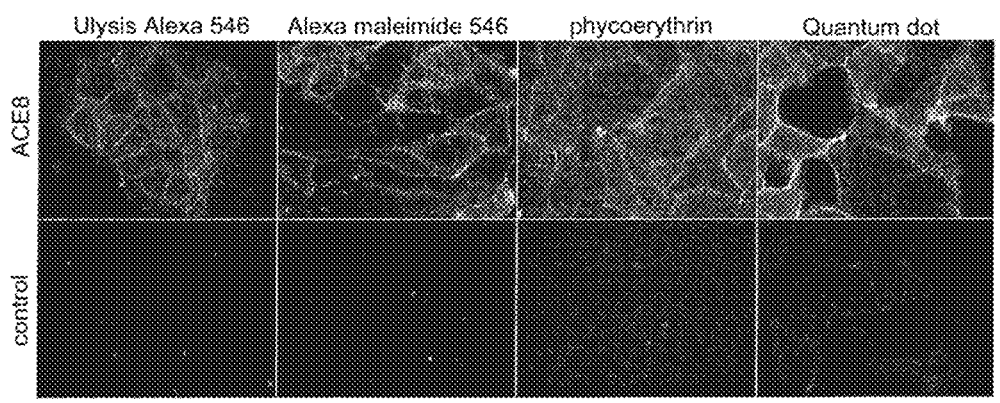
FIG. 12: Use of the Aptamers in Microscopy

Using various techniques for direct or nondirect labeling of the ACE8 aptamer (phycoerythrin, alexafluor, Quantum. Dots), the inventors also showed that the ACE8 aptamer can be used very simply in microscopy on live cells (FIG. 12).

Example 3

Figure 13:
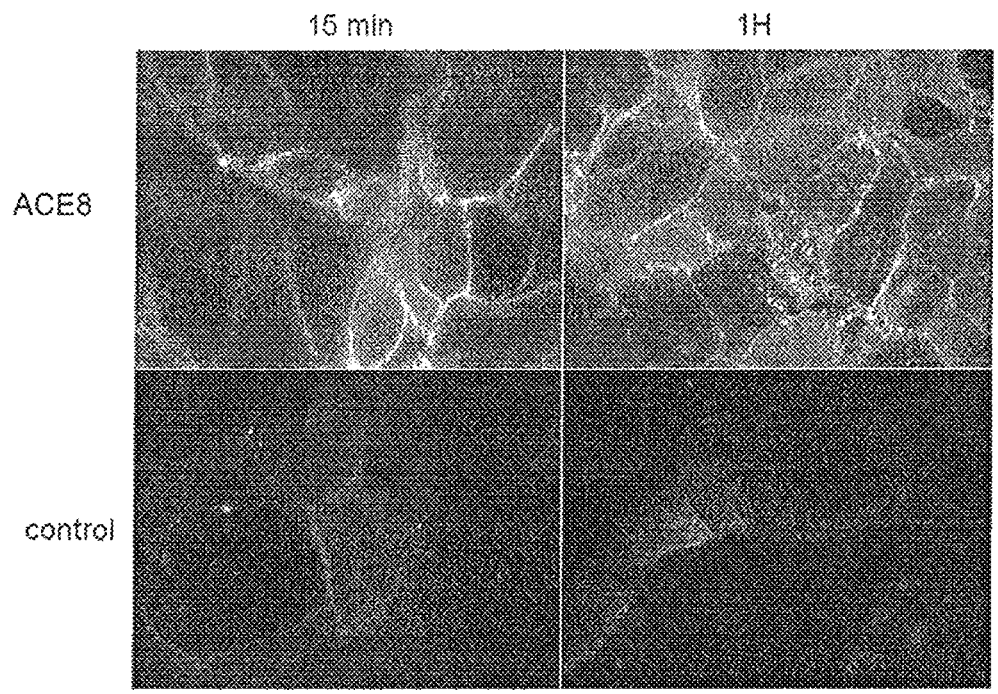
FIG. 13: Targeting of Nanoparticles Using the ACE8 Aptamer

Use of the ACE8 Aptamer as a Molecule for Targeting of Nanoparticles and Internalization of Compounds The ACE8 aptamer retained its targeting properties once grafted at the surface of a Quantum Dot; this demonstrates that it could be used to specifically target other nanoparticles of use for imaging or therapy. Since the ACE8 aptamer is endocytosed by cells over time, it is also capable of causing these nanoparticles or other compounds, such as pharmacological compounds or contrast agents, to enter cells (FIG. 13).

Example 4

Use of the ACE8 Aptamer in Flow Cytometry

Figure 14:
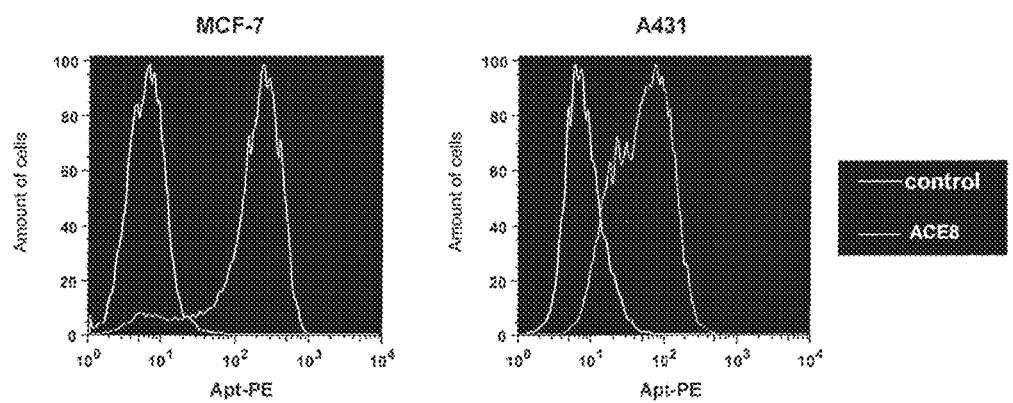
FIG. 14: Use of the ACE8 Aptamer in Flow Cytometry (FACS)

The fluorescently labeled ACE8 aptamer was used in flow cytometry (FCM) after incubation on MCF-7 cells and on A-431 cells at a concentration of 5 nM (FIG. 14). A clear increase in the fluorescence intensity of the cells can be seen when they are incubated with the ACE8 aptamer, compared with the cells incubated with the control sequence (SEQ ID NO: 11). Furthermore, this increase in intensity is more or less considerable depending on the amount of target at the surface of the cells. These results are in agreement with the binding data: the fluorescence intensity of the MCF-7 cells is greater than that of the A-431 cells after incubation with the ACE8 aptamer, and the MCF-7 cells have a greater number of targets than the A-431 cells.

Example 5

Use of the ACE8 Aptamer in In Vivo Imaging

Figure 15:
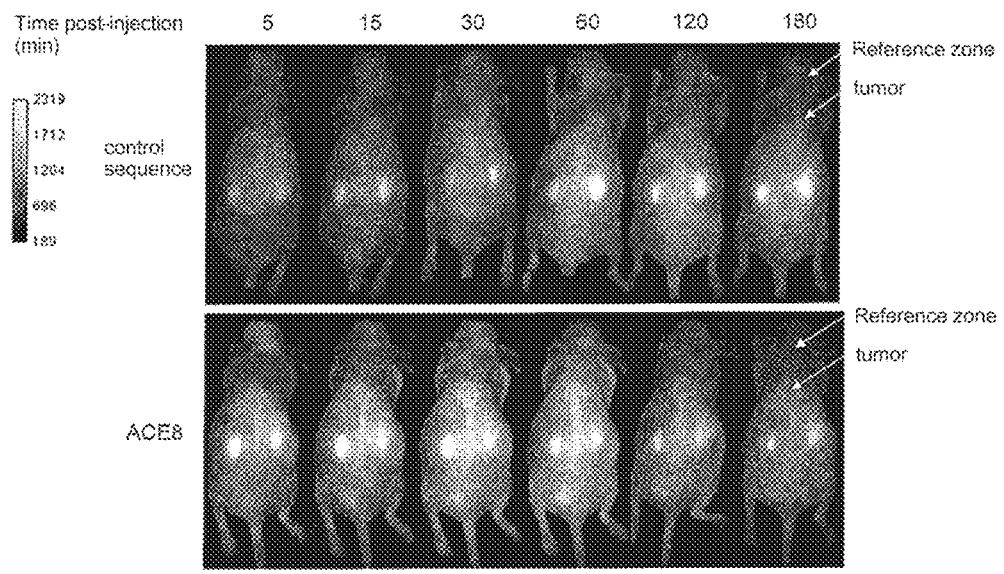
FIG. 15: Use of the ACE8 Aptamer in In Vivo Planar Fluorescent Imaging

The ACE8 aptamer was used for in vivo tumor imaging. The fluorescently labeled ACE8 aptamer was injected intravenously into nude mice developing tumors resulting from subcutaneous xenografts of MCF-7 cells. The biodistribution of the aptamer was measured by fluorescent imaging. Using in vivo semi-quantitative imaging (FIG. 15), the inventors were able to observe that the aptamer diffuses very quickly from the blood compartment and is very quickly eliminated in the urine and partially via the hepatobiliary route. Interestingly, the comparison of the signal in the tumor relative, to a reference zone at the level of the head of the animal (tumor/internal reference ratio) increases more rapidly for the ACE8 aptamer than for a control sequence (SEQ ID NO: 11), and a significant difference is observed 15 minutes after the injection (1.61+/−0.15 compared with 1.18+/−0.04, respectively, see Table 3). After 15 minutes, this ratio gradually increases, but in a similar manner for the ACE8 aptamer and the control sequence (FIG. 15 and Table 1).

TABLE 3

Ratio of signal in the tumor/internal reference over time

| Time (min) | Tumor/internal reference ratio Control sequence | Tumor/internal reference ratio ACE8 | Student's statistical test (P < 0.05) |
|---|---|---|---|
| 5 | 1.10 +/− 0.12 | 1.34 +/− 0.14 | Ns |
| 10 | 1.17 +/− 0.10 | 1.48 +/− 0.16 | Ns |
| 15 | 1.18 +/− 0.04 | 1.61 +/− 0.15 | * |
| 30 | 1.32 +/− 0.08 | 1.73 +/− 0.22 | * |
| 60 | 1.42 +/− 0.09 | 1.79 +/− 0.21 | * |
| 90 | 1.43 +/− 0.18 | 1.85 +/− 0.15 | * |
| 120 | 1.52 +/− 0.11 | 1.90 +/− 0.17 | * |
| 150 | 1.54 +/− 0.15 | 1.96 +/− 0.28 | * |
| 180 | 1.57 +/− 0.17 | 1.97 +/− 0.29 | * |

The fluorescence signal measured in the tumor was divided by the fluorescent signal measured in a zone at the level of the head of the animal (see FIG. 15). This ratio was measured at various times in triplicate.
* corresponds to a significant difference in the ratio between ACE8 and the control sequence measured by means of a student's test with P < 0.05.
Ns: not significant.

This result demonstrates that the ACE8 aptamer must rapidly bind to its target in the tumor.

Figure 16:
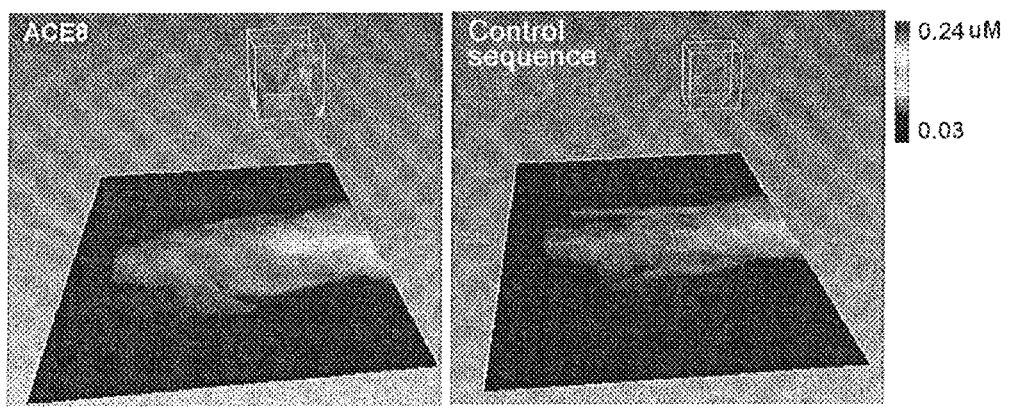
FIGS. 16 and 17: Use of the ACE8 Aptamer in In Vivo 3D Fluorescent Imaging
Figure 17:
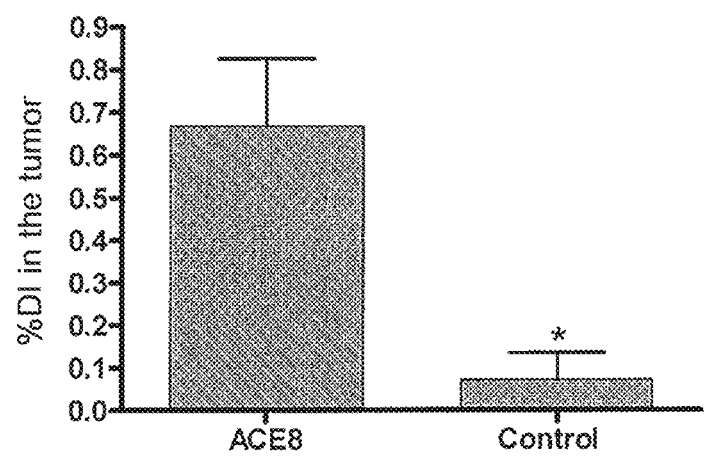

In order to better quantify the biodistribution of the aptamer in the tumor, measurements were carried out by fluorescence tomography at the time 3 h post-injection (FIGS. 16 and 17). It was thus possible to measure that approximately 0.67%±0.27 of the injected dose of aptamer is present in the tumor 3 h post-injection, compared with 0.07%±0.11 for the control sequence.

Example 6

Use of the ACE8 Aptamer as an Angiogenesis Inhibitor

Figure 18:
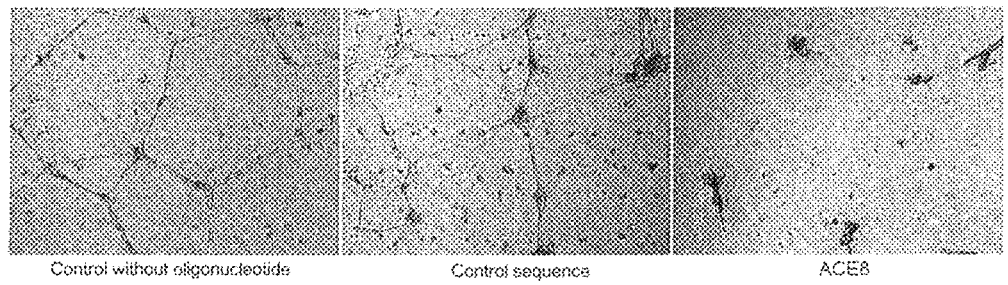
FIGS. 18 and 19: Use of the ACE8 Aptamer as an Angiogenesis Inhibitor
Figure 19:
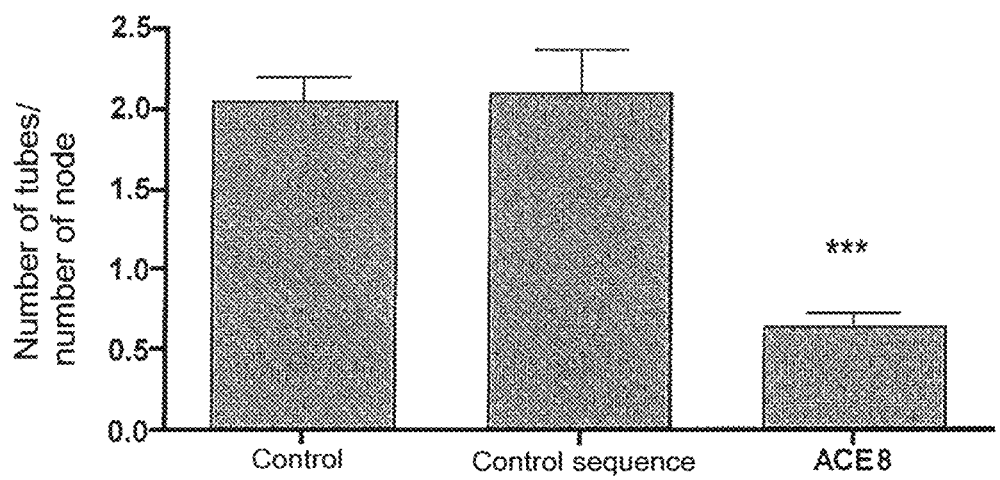

The use of the ACE8 aptamer as an angiogenesis inhibitor was validated on an in vitro model of endothelial tube formation. Human umbilical vein endothelial cells (HUVECs) were cultured, with or without oligonucleotide (5 µM), on Matrigel™ (Becton-Dickinson) in a medium with a low growth hormone content containing 2% (v/v) of fetal calf serum and basic fibroblast growth factor (bFGF at 3 ng/ml). Under these conditions, the HUVECs form a network of endothelial tubes which can be observed by microscopy and represents a proven in vitro model of angiogenesis. The formation of this network is not affected by the presence of the control sequence. On the other hand, the ACE8 aptamer strongly inhibits the formation of this network (FIGS. 18 and 19).

Example 7

Use of the ACE8 Aptamer to Screen for Molecules which can Bind to Annexin 2

It was shown that it is possible to use the ACE8 aptamer to screen for molecules which can bind to annexin 2 by means of competition experiments. For this, the inventors studied whether such a competition took place between the aptamers.

Figure 20:
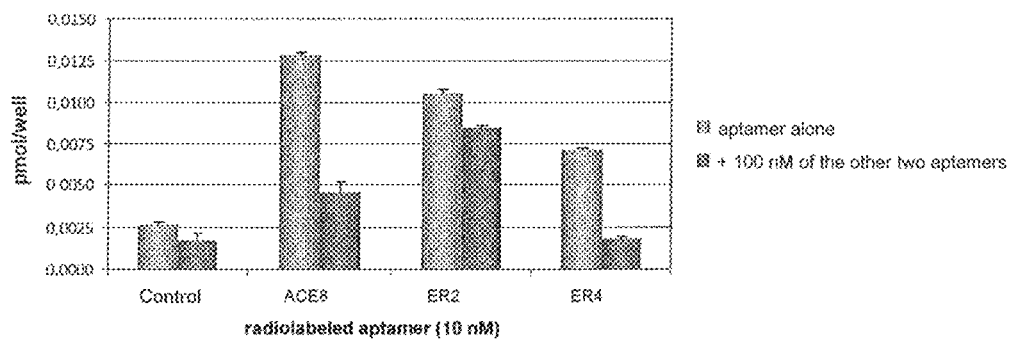
FIG. 20: Use of the ACE8 Aptamer for Screening for Molecules which can Bind to Annexin 2

Thus, when the radiolabeled ER2 aptamer is incubated in the presence of the ACE8 and ER4 aptamers, the affinity is the same as the aptamer alone, thereby signifying that the ER2 aptamer does not compete with the ACE8 and ER4 aptamers. On the other hand, when the ACE8 aptamer is incubated in the presence of the other two, a decrease in affinity is observed. The same is true for the ER4 aptamer (FIG. 20).

The results of these experiments show competition between the ACE8 and ER4 aptamers, suggesting that the annexin 2 also appears to be the target of the EPA aptamer.

Figure 21:
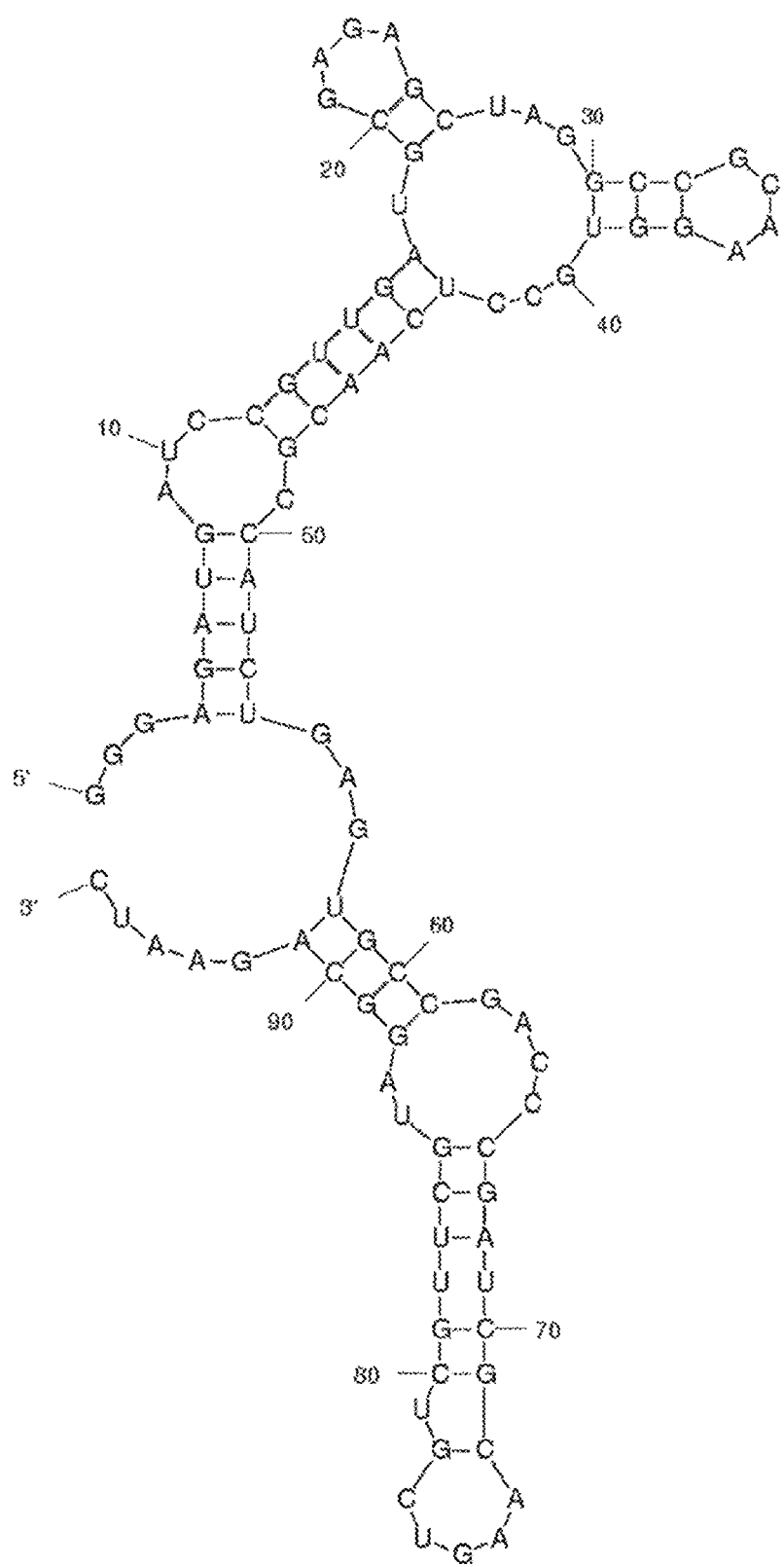
FIG. 21: ER4 Aptamer Structure Prediction

The ER4 aptamer is represented in FIG. 21 and consists of the sequence:

```
                                              (SEQ ID NO: 4)
5' GGGAGAUGAUCCGUUGAUGCGAGAGCUAGGCCGCAAGGUGCCUCAA

CGCCAUCUGAGUGCCGACCCGAUCGCAAGUCGUCGUUCGUAGGCAGAAU

C 3'.
```

Example 8

Figure 22:
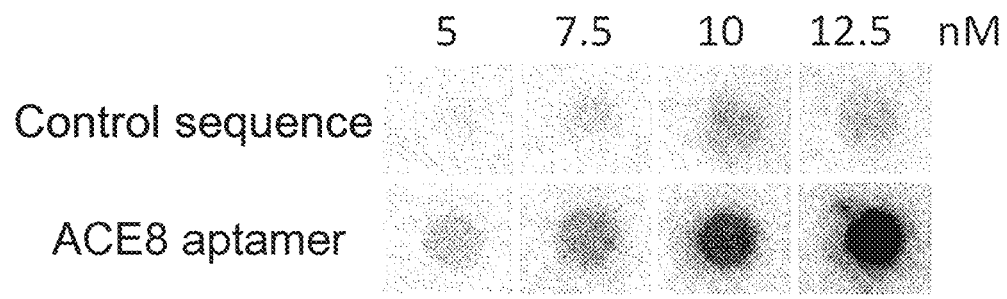
FIGS. 22 and 23: Measurement of the Affinity of the ACE8 Aptamer for the Annexin 2/S100A10 Heterotetrameric Complex The ACE8 aptamer and a control sequence were radiolabeled at the 5' end with phosphorus 32 ($[^{32}P]$). 1 pmol of ACE8 aptamer or of the control sequence was then preincubated with various concentrations of an annexin 2/S100A10 heterotetrameric complex. The fraction of ACE8 aptamer or of control sequence bound to the annexin 2/S100A10 heterotetramer was retained on a nitrocellulose filter and analyzed and quantified using a Storm PhosphorImager.
Figure 23:
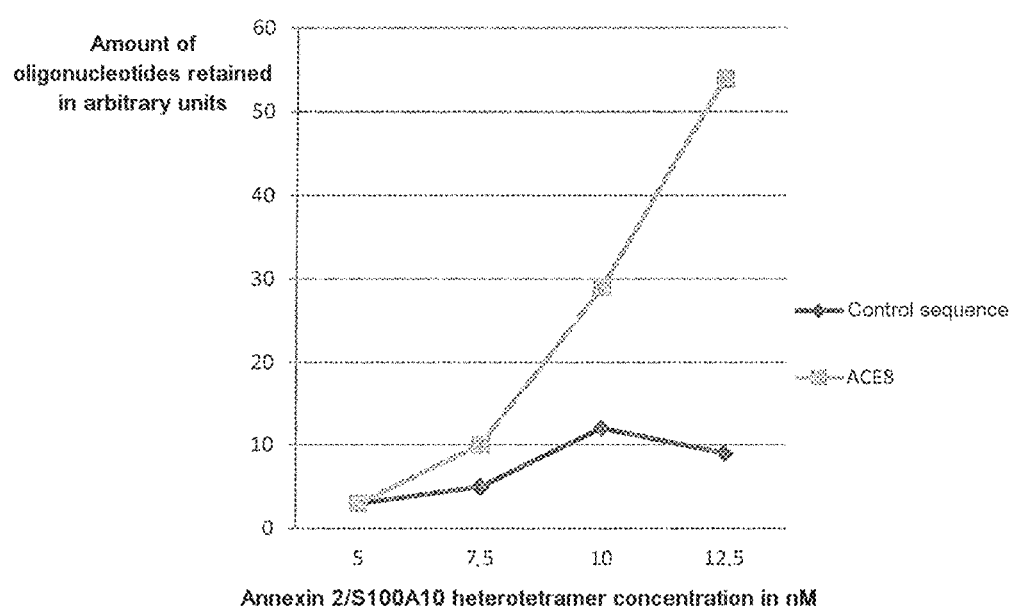

Measurement of the Affinity of the ACE8 Aptamer for the Annexin 2/S100A10 Heterotetrameric Complex The inventors also showed specific and direct binding of ACE8 to the annexin 2/S100A10 heterotetrameric complex (FIGS. 22 and 23).

For this, the oligonucleotides (ACE8 aptamer or control sequence (SEQ ID NO: 11)) were dephosphorylated at their 5' end for 30 min at 37° C. with 2.5 U of Antarctic Phosphatase (New-England Biolabs) per nmol of 2'F-Py RNA. After inactivation of the enzyme at 88° C. for 15 min, the 2'F-Py RNA was precipitated with ethanol in the presence of 5 µl/ml of a neutral coprecipitant (Linear Polyacrylamide or LPA) (Ambion). The oligonucleotides were then labeled with ATP [gamma-$^{32}$P] using T4 kinase (invitrogen) according to the supplier's instructions. The 2'F-Py RNAs (2.3 MBq, i.e. 63nCi/pmol or 63nCi/pmol$^{-1}$) were subsequently purified by exclusion chromatography (Bio-Spin Sp30 Chromatography Columns (Biorad)). 1 pmol of ACE8 aptamer or of the control sequence was then preincubated for 30 min. at ambient temperature with various concentrations (0, 5, 7.5, 10 and 12.5 nM) of an annexin 2/S100A10 heterotetrameric complex (two annexin 2 proteins with two S100A10 proteins) purified from bovine lung (Interchim, France, ref.: A80109B). The preincubation was carried out in 200 µl of RPMI 1640 medium (invitrogen) in the presence of 3 µg of yeast transfer RNA (Sigma-Aldrich), which represents an amount of RNA 100 times greater than the aptamer or the control sequence. The mixture was then filtered through 0.45µ HAWP nitrocellulose membranes (Millipore) and the membrane was washed by filtration of 5 volumes of 200 µl of RPMI 1640. The nitrocellulose membrane makes it possible to retain the proteins and to allow the RNAs to pass through. Thus, only the fraction of ACE8 aptamer or control sequence bound to the annexin 2/S100A10 heterotetramer is retained on the nitrocellulose filter. This filter is then dried and the fraction of ACE8 aptamer or of control sequence bound to the annexin 2/S100A10 heterotetramer can be quantified using a Storm PhosphorImager (GE Healthcare).

The results (FIGS. 22 and 23) demonstrate that the ACE8 aptamer interacts with the annexin 2/S100A10 heterotetramer with a very strong affinity compared with a control sequence.

The invention claimed is:

1. An aptamer comprising a nucleic acid comprising, or consisting of SEQ ID NO: 1 or 2, or a sequence comprising, or consisting of, at least 25 consecutive nucleotides of a sequence having at least 80% identity with SEQ ID NO: 1 or 2, wherein the nucleic acid consisting of this sequence binds to annexin 2.

2. The aptamer as claimed in claim 1, comprising a nucleic acid consisting of SEQ ID NO: 3 or 4.

3. The aptamer as claimed in claim 1, wherein the nucleic acid is linked to at least one additional group.

4. The aptamer as claimed in claim 3, wherein the additional group is selected from the group consisting of a detectable label, a pharmacological compound, and a compound capable of modifying the pharmacokinetic characteristics of a nucleic acid to which it is linked.

5. The aptamer as claimed in claim 1, consisting of the nucleic acid and of at least one additional group.

6. A pharmaceutical or diagnostic composition comprising, as active substance, at least one aptamer as defined in one of claims 1 to 5, in combination with at least one pharmaceutically acceptable vehicle.

7. An in vitro method for detecting or quantifying annexin 2 in a biological sample, comprising:
   bringing the biological sample into contact with an aptamer as defined in claim 1;
   quantifying or detecting the presence or absence of aptamer bound in the sample;
   deducing therefrom the amount, or the presence or absence, of annexin 2 in the sample.

8. The method as claimed in claim 7, wherein the detection of aptamer bound in the sample is carried out by performing a PCR intended to amplify the aptamer.

9. A method for screening for annexin 2 ligands, comprising:
   i. bringing together annexin 2 and, concomitantly or successively, a ligand to be screened and an aptamer as defined in claim 1;

ii. determining the amount of aptamer bound to annexin 2; and iii. deducing therefrom whether the ligand is an annexin 2 ligand.

10. A method for the diagnosis of a cancer in an individual, comprising the following steps:
   i. administering an aptamer as defined in claim 1 to the individual;
   ii. detecting, quantifying and/or localizing the aptamer in the individual or a part of the individual; and
   iii. deducing therefrom whether the individual is suffering from a cancer.

11. A method for detecting, quantifying or localizing annexin 2, in an individual or a part of an individual, comprising the following steps:
   i. administering an aptamer as defined in claim 1 to the individual;
   ii. detecting, quantifying and/or localizing the aptamer in the individual or a part of the individual; and
   iii. deducing therefrom the presence or absence, the amount, and/or the localization of annexin 2 in the individual or the part of the individual.

* * * * *

SEQUENCE LISTING

```
<160> NUMBER OF SEQ ID NOS: 11

<210> SEQ ID NO 1
<211> LENGTH: 48
<212> TYPE: RNA
<213> ORGANISM: Artificial sequence
<220> FEATURE:
<223> OTHER INFORMATION: Central sequence of aptamer ACE8

<400> SEQUENCE: 1
ggaacgcaag aacugaggcc augaggcgcc uucccuugcu caggacgc        48

<210> SEQ ID NO 2
<211> LENGTH: 49
<212> TYPE: RNA
<213> ORGANISM: Artificial sequence
<220> FEATURE:
<223> OTHER INFORMATION: Central sequence of aptamer ER4

<400> SEQUENCE: 2
agcuaggccg caaggugccu caacgccauc ugagugccga cccgaucgc       49

<210> SEQ ID NO 3
<211> LENGTH: 95
<212> TYPE: RNA
<213> ORGANISM: Artificial sequence
<220> FEATURE:
<223> OTHER INFORMATION: Sequence of aptamer ACE8

<400> SEQUENCE: 3
gggagaugau ccguugaugc gagggaacgc aagaacugag gccaugaggc gccuucccuu    60
gcucaggacg caagucgucg uucguaggca gaauc                              95

<210> SEQ ID NO 4
<211> LENGTH: 96
<212> TYPE: RNA
<213> ORGANISM: Artificial sequence
<220> FEATURE:
<223> OTHER INFORMATION: Sequence of aptamer ER4

<400> SEQUENCE: 4
gggagaugau ccguugaugc gagagcuagg ccgcaaggug ccucaacgcc aucugagugc    60
cgacccgauc gcaagucguc guucguaggc agaauc                             96

<210> SEQ ID NO 5
<211> LENGTH: 339
<212> TYPE: PRT
<213> ORGANISM: Homo sapiens

<400> SEQUENCE: 5

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
```

```
                35                  40                  45
Lys Gly Val Asp Glu Val Thr Ile Val Asn Ile Leu Thr Asn Arg Ser
 50                  55                  60

Asn Ala Gln Arg Gln Asp Ile Ala Phe Ala Tyr Gln Arg Arg Thr Lys
 65                  70                  75                  80

Lys Glu Leu Ala Ser Ala Leu Lys Ser Ala Leu Ser Gly His Leu Glu
                 85                  90                  95

Thr Val Ile Leu Gly Leu Leu Lys Thr Pro Ala Gln Tyr Asp Ala Ser
                100                 105                 110

Glu Leu Lys Ala Ser Met Lys Gly Leu Gly Thr Asp Glu Asp Ser Leu
                115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
                180                 185                 190

Gln Asp Ala Arg Asp Leu Tyr Asp Ala Gly Val Lys Arg Lys Gly Thr
                195                 200                 205

Asp Val Pro Lys Trp Ile Ser Ile Met Thr Glu Arg Ser Val Pro His
210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
                260                 265                 270

Arg Leu Tyr Asp Ser Met Lys Gly Lys Gly Thr Arg Asp Lys Val Leu
                275                 280                 285

Ile Arg Ile Met Val Ser Arg Ser Glu Val Asp Met Leu Lys Ile Arg
290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 6
<211> LENGTH: 24
<212> TYPE: DNA
<213> ORGANISM: Artificial sequence
<220> FEATURE:
<223> OTHER INFORMATION: PCR primer

<400> SEQUENCE: 6
gattctgcct acgaacgacg actt                                        24

<210> SEQ ID NO 7
<211> LENGTH: 23
<212> TYPE: DNA
<213> ORGANISM: Artificial sequence
<220> FEATURE:
<223> OTHER INFORMATION: PCR primer

<400> SEQUENCE: 7
```

```
gggagatgat ccgttgatgc gag                                          23

<210> SEQ ID NO 8
<211> LENGTH: 97
<212> TYPE: DNA
<213> ORGANISM: Artificial sequence
<220> FEATURE:
<223> OTHER INFORMATION: Sequence of aptamer ER2

<400> SEQUENCE: 8
gggagatgat ccgttgatgc gagcagagcc gctggcgact tattccaaca gtcgccccca   60 caaccttgt cccaagtcgt cgttcgtagg cagaatc                            97

<210> SEQ ID NO 9
<211> LENGTH: 21
<212> TYPE: RNA
<213> ORGANISM: Artificial sequence
<220> FEATURE:
<223> OTHER INFORMATION: Anti-annexine 2 siRNA

<400> SEQUENCE: 9
ucauccacac cuuuggucuu u                                            21

<210> SEQ ID NO 10
<211> LENGTH: 21
<212> TYPE: RNA
<213> ORGANISM: Artificial sequence
<220> FEATURE:
<223> OTHER INFORMATION: Anti-annexine 2 siRNA

<400> SEQUENCE: 10
ucagcaucaa aguuaguauu u                                            21

<210> SEQ ID NO 11
<211> LENGTH: 97
<212> TYPE: DNA
<213> ORGANISM: Artificial sequence
<220> FEATURE:
<223> OTHER INFORMATION: Aptamere control sequence

<400> SEQUENCE: 11
gggagatgat ccgttgatgc gaggatccct acgacctcgt agcacacaca taggtgcact   60
cacccggctg accaagtcgt cgttcgtagg cagaatc                           97
```